United States Patent [19]

Mészáros et al.

[11] Patent Number: 4,460,771
[45] Date of Patent: Jul. 17, 1984

[54] ANTIPHLOGISTIC AND ANTICOAGULANT CONDENSED PYRIMIDINE DERIVATIVES

[75] Inventors: Zoltán Mészáros; József Knoll; Péter Szentmiklósi; István Hermes; Ágnes Horváth; Sándor Virág; Lelle Vasvári nee Debreczy; Agoston David, all of Budapest, Hungary

[73] Assignee: Chinoin Gyogyszer es Vegyeszeti Termekek Gyara R.T., Budapest, Hungary

[21] Appl. No.: 742,464

[22] Filed: Nov. 17, 1976

[30] Foreign Application Priority Data

Nov. 27, 1975 [HU] Hungary .................. CI 1623

[51] Int. Cl.$^3$ .................. C07D 471/04; A61K 31/505
[52] U.S. Cl. .................. 544/282; 424/251; 544/252
[58] Field of Search .................. 260/256.4 F; 544/282

[56] References Cited

U.S. PATENT DOCUMENTS

| | | | |
|---|---|---|---|
| 3,585,198 | 6/1971 | Meszaros et al. | 544/282 |
| 3,642,797 | 2/1972 | Lesher | 544/282 |
| 3,960,863 | 6/1976 | Sato et al. | 260/256.4 F |
| 4,022,897 | 5/1977 | Yale et al. | 260/256.4 F |
| 4,066,766 | 1/1978 | Kadin | 260/256.4 F |
| 4,122,274 | 10/1978 | Juby | 544/282 |
| 4,192,944 | 3/1980 | Juby | 544/282 |
| 4,209,622 | 6/1980 | Meszaros et al. | 544/282 |

OTHER PUBLICATIONS

"The Pharmacology of 1,6-Dimethyl-3-carbethoxy-4-oxo-6,7,8,9-tetrahydrohomopyrimidazol-methylsulphate (MZ-144), a New, Potent, Non–Narcotic Analgesic" Knoll et al., Arzneimittel-Forschung, vol. 21, No. 5, pp. 717–727, (1971).

Primary Examiner—Mary C. Lee
Assistant Examiner—James H. Turnipseed
Attorney, Agent, or Firm—Karl F. Ross; Herbert Dubno

[57] ABSTRACT

New optionally racemic or optically active pyrimido(1-,2a) heterocyclic compounds of the formula

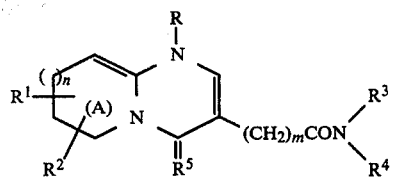

wherein
m is 0, 1 or 2,
n is 0, 1 or 2,
R is an alkyl group containing one to six carbon atoms,
$R^1$ is hydrogen, alkyl containing one to six carbon atoms,
$R^2$ is hydrogen, alkyl containing one to six carbon atoms, optionally substituted amino, optionally substituted hydroxy, carboxy or a group derived from a carboxylic acid or
$R^1$ and $R^2$ together form a —(CH=CH)$_2$— group attached to the two adjacent carbon atoms of the ring A and the broken line represents a chemical bond,
$R^3$ is hydrogen, optionally substituted alkyl, optionally substituted aryl, optionally substituted aralkyl, optionally substituted heterocycle, optionally substituted cycloalkyl, optionally substituted acyl or optionally substituted hydroxy,
$R^4$ is hydrogen, optionally substituted alkyl, optionally substituted aryl, optionally substituted aralkyl, optionally substituted heterocycle, optionally substituted cycloalkyl, optionally substituted acyl or
$R^3$ and $R^4$ together with the nitrogen can form an optionally substituted five-, six- or seven-membered ring, which can contain a further heteroatom or heteroatoms,
$R^5$ is oxygen or an optionally substituted imino group are disclosed as well as a process for the preparation thereof.

4 Claims, No Drawings

ANTIPHLOGISTIC AND ANTICOAGULANT CONDENSED PYRIMIDINE DERIVATIVES

The invention relates to new optionally racemic or optically active pyrimido (1,2a) heterocyclic compounds of the formula

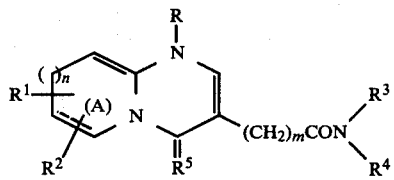

wherein
m is 0, 1 or 2,
n is 0, 1 or 2
R is an alkyl group containing one to six carbon atoms,
$R_1$ is hydrogen, alkyl containing one to six carbon atoms,
$R_2$ is hydrogen, alkyl containing one to six carbon atoms, substituted or unsubstituted amino, substituted or unsubstituted hydroxy, carboxy or a group derived from a carboxylic acid or
$R_1$ and $R_2$ together form a —(CH=CH)$_2$— group attached to the two adjacent carbon atoms of the ring A and the broken line represents a chemical bond;
$R_3$ is hydrogen, substituted or unsubstituted alkyl, substituted or unsubstituted aryl, substituted or unsubsituted aralkyl, substituted or unsubstituted heterocylic moieties substituted or unsubstituted cycloaklyl, or substituted substituted acyl or substituted or unsubstituted hydroxy,
$R_4$ is hydrogen, substituted or unsubstituted alkyl, substituted or unsubstituted aryl, substituted or unsubstituted aralkyl, substituted or unsubstituted heterocylic moieties substituted or unsubstituted cycloalkyl, substituted or unsubstituted acyl or
$R_3$ and $R_4$ together with the nitrogen can form substituted or unsubstituted five-, six- or seven-membered ring, which can contain a further heteroatom or heteroatoms,
$R_5$ is oxygen or substituted or unsubstituted imino group.

This invention further provides novel processes for the preparation of the new pyrimido (1,2a) heterocyclic compounds of the formula I.

The new compounds are prepared (a) directly from the optionally racemic or optically active pyrimido(1,2a) *heterocyclic quaternary compound of the formula*

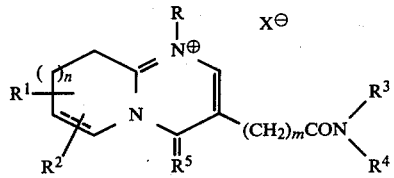

wherein
m, n, R, $R^1$, $R^2$, $R^3$, $R^4$, $R^5$ and the dotted line are as defined above and X is an anion
by reacting the compound of the formula II with an inorganic base, a salt thereof or with an organic base in the presence of an aprotic solvent or without any solvent, or (b) from the optionally racemic or optically active pyrimido(1,2a) heterocyclic quaternary compound of the formula II in a protic solvent through the pyrimido(1,2a) heterocycle of the formula

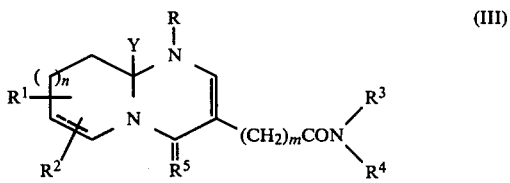

wherein m, n, R, $R^1$, $R^2$, $R^3$, $R^4$, $R^5$ and the dotted line are as defined above Y is hydroxy, alkoxy, nitrile or substituted or unsubstituted amino, formed by reacting the compound of the formula II with an organic base or an inorganic base or a salt of the inorganic base, by splitting off HY from the molecule of the formula III or (c) by reacting the optionally racemic or optically active pyrimido(1,2a) heterocycle of the formula

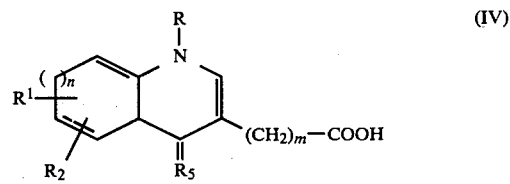

wherein m, n, R, $R^1$, $R^2$ and $R^5$ and the dotted line are as defined above, with an optically active amine of the formula V

wherein $R^3$ and $R^4$ are as defined above.

The method (a) is preferably carried out at 0° to 200° C.

As aprotic solvents, aromatic hydrocarbons, preferably benzene, halogenated hydrocarbons; preferably chlorobenzene, chloroform, carbon tetrachloride; aliphatic ketones, preferably acetone, methyl ethyl ketone; ethers, preferably diethylether, dioxane; esters, preferably ethylformate, ethylacetate or a mixture of the above solvents may be employed.

As an organic base trialkylamines, preferably triethylamine, trimethylamine, tributylamine and nitrogen containing aromatic heterocyclic compounds, such as pyridine may be used. If desired, an excess of the organic base may serve as an aprotic solvent.

As a salt of an inorganic base alkali metal hydrogen carbonates, preferably sodium or potassium bi-carbonate, alkali metal carbonates, preferably sodium or potassium carbonate, a salt of an alkali metal with an organic acid such as sodium or potassium acetate or alkali earth metal carbonates, preferably calcium carbonate may be used.

The method (b) is preferably performed at temperatures of 0° to 200° C.

As protic solvents, water; alcohols such as ethanol, n-propanol, isopropanol, n-butanol, glycol; or a mixture of said solvents can be employed.

As a solvent the mixtures of the solvents enumerated for both methods (a) and (b) may also be used.

As organic bases trialkyl-, dialkyl-, alkylamines, preferably triethylamine, diethylamine, n-butylamine, tetraalkylammoniumhydroxide, preferably tetraethylammoniumhydroxide and nitrogen containing heterocyclic compounds, such as pyridine or piperidine may be employed.

As inorganic bases alkali metal hydroxides, preferably sodium hydroxide, potassium hydroxide; alkali metal carbonates, preferably sodium carbonate, potassium carbonate; alkali metal bicarbonates preferably sodium bicarbonate, potassium bicarbonate; alkali earth metal bydroxides, such as calcium hydroxide; alkali earth metal carbonates, such as calcium carbonate; alkali metal cyanides; ammonium hydroxide; ammonium carbonate; ammonium bicarbonate or gaseous ammonia may be used.

Working according to methods (a) and (b), either the compound of the formula I is precipitated from the reaction mixture and can be removed by filtration, or after evaporation the residue is recrystallized from a suitable solvent and the compound of the formula I is obtained.

According to one of the embodiments of method (c) a compound of the formula IV is reacted with an amine of the formula V by dissolving the compound of the formula IV in an organic solvent, preferably in chlorinated hydrocarbons, particularly in chloroform or in ethers, such as dioxane, tetrahydrofurane and trialkyl amine, preferably triethylamine or tributylamine is added, whereafter an acid halide, preferably trimethyl acetic acid halide, such as trimethyl acetic acid chloride or chloroformic acid ester, preferably chloroformic acid methyl, ethyl or isopropylester is added dropwise to the obtained solution at −30° C. to 50° C., preferably at −20° C. to 0° C. The amine of the formula V is then added dropwise, if desired, dissolved in the solvent given above or when using the acid addition salt thereof it is added together with trialkylamine, such as triethylamine or tributylamine, the reaction mixture is then stirred at a temperature range given above, the mixture is shaken out with an aqueous solution of sodium bicarbonate and then with water whereafter it is allowed to warm to room temperature.

The reaction mixture is evaporated after drying and the residue is recrystallized from a suitable solvent.

According to another feature of method (c) a compound of the formula IV is reacted with an amine of the formula V preferably in an organic solvent in the presence of a water-binding agent. Preferred water binding agents are, for example, carbodiimides such as dicyclohexyl-carbodiimide. In such cases the reaction is preferably carried out in the presence of 1-hydroxy-benzotriazole, N-hydroxy-succinic imide or pentachlorophenol, as in the presence of those substances side reactions are minimized.

As solvents aromatic hydrocarbons, such as benzene, chlorinated hydrocarbons, such as chloroform, chlorobenzene, ketones, such as acetone, methylethylketone, ethers, such as dioxane, tetrahydrofurane, esters such as ethyl acetate are preferred or when using carbodiimide soluble in aqueous alcohol, a mixture of water and alcohol or a mixture of the said solvents can be employed.

The reaction is carried out at temperatures of 20° to 100° C. After the reaction is completed, the precipitated urea is removed by filtration and the residue obtained after the evaporation of the filtrate is recrystallized from a suitable solvent and thus the pyrimido(1,2a) heterocycle of the formula I is obtained.

The pyrimido(1,2a) heterocyclic compounds of the formulae II and IV can be prepared according to Hungarian Patent Specifications Nos: 156,119, 158,085, 162,384, 162,373, 166,577 and Dutch Patent Specification No: 7,212,286, and the amines of the formula V are available.

The invention also includes the racemic and optically active forms of the pyrimido(1,2a)heterocyclic compounds of the formula I, this is only possible, if at least one of $R^1$ and $R^2$ is different from hydrogen and $R^1$ and $R^2$ together do not form a—(CH=CH)— chain. The optically active compounds of the formula I may be obtained by resolving the racemic compounds of the formula I by methods known in the art, or optically active starting materials of the formula II respectively IV are used.

The term "optionally substituted amino" means an acylamino, preferably acetylamino alkylamino, such as methylamino, ethylamino, dialkylamino, preferably dimethylamino or diethylamino group, the term "optionally substituted hydroxy" indicates an alkoxy group, such as methoxy, ethoxy, aralkoxy such as benzyloxy group, the term "optionally substituted alkyl group" means a straight or branched chain alkyl of one to 6 carbon atoms, optionally bearing an optionally substituted amino, optionally substituted hydroxy, keto, optionally substituted aryl, carboxy or a group derived from a carboxylic acid, the term "substituted aryl group" as used herein means phenyl or naphthyl groups, optionally substituted by optionally substituted amino, alkyl of one to 6 carbon atoms, optionally substituted hydroxy, carboxy or a group derived from carboxylic acid or nitro groups, the term "optionally substituted aralkyl group" as used herein means preferably alkyl of one to 6 carbon atoms, optionally substituted hydroxy, optionally substituted amino, nitro, carboxy groups or a group derived from a carboxylic acid and the term "optionally substituted heterocyclic group" means five-, six- or seven-membered partially or completely saturated mono- resp. bicyclic heterocycles, containing nitrogen, oxygen, sulphur atoms or nitrogen and oxygen, optionally substituted by alkyl, acyl or alkoxy of one to 6 carbon atoms and the term "optionally substituted cycloalkyl group" means a five-, six- or seven-membered cycloalkyl group, optionally substituted by an alkyl group of one to 6 carbon atoms.

The compounds of the formula I possess a significant degree of pharmacological activity and compounds of the formula I are particularly effective as antiphlogistics, PG antagonists, inhibit the blood platelet aggregation and exhibit analgesic activity or show some other favorable effects on the central nervous system.

The pharmacological and toxicological tests show, under various conditions, a significant degree of activity and low toxicity.

The test results are demonstrated in connection with 3-carbamoyl-1,6-dimethyl- 4-oxo-1,6,7,8-tetrahydro-4H-pyrido(1,2a)pyrimidine (identified as CH-105). In our investigations antiphlogistics known from the art such as Phenylbutazone, Aspirin, Indomethacin, Mebron and Amidazophenum were used for comparison.

The antiphlogistic activity of CH-105 was tested by a method known in the art that is the rat paw oedema method (Domenju, R.: Ann. Univ. Saraviensis 1, 317, 1953).

The test results obtained by various methods and the outstanding activity of CH-105 are shown in Table 1.

TABLE 1

| Substance | Dose mg/kg | Oedema inhibiting effect in % | | |
|---|---|---|---|---|
| | | 1 hour | 2 hours | 24 hours |
| | | after the administration of the substance | | |
| CH-105 | 100 | 25 | 34 | |
| | 300 | 45 | 52 | 8 |
| Mebron | 100 | 8 | 22 | |
| | 300 | 25 | 25 | 3 |
| Phenylbutazone | 100 | 2 | 2 | |
| | 200 | 11 | 10 | 3 |

According to the latest data in the literature the prostaglandins play an important role in the formation of inflammations (Vane, J.R.: Prostaglandins in inflammatory response, In.: Inflammation, 1972. N.Y. Academic Press). Thus it seemed to be appropriate to test the effectivity of the substance of the invention in the inflammation response caused by prostaglandin $E_1$ and $E_2$ particularly from the point of view of the vessel wall permeability, which plays an important role in inflammation.

TABLE 2

| Substance | Dose mg/kg | Oedema inhibition (%) | | Vessel wall permeability inhibition % | |
|---|---|---|---|---|---|
| | | $PGE_1$ | $PGE_2$ | $PGE_1$ | $PGE_2$ |
| CH-105 | 200 | 30 | 31 | 40 | 35 |
| | 500 | 42 | 45 | 40 | 50 |
| Aspirin | 200 | 41 | 20 | 30 | 25 |
| | 500 | 45 | 54 | 42 | 50 |
| Phenylbutazone | 100 | 5 | 10 | 10 | 5 |
| | 200 | 15 | 28 | 20 | 20 |

The data of the table 2 show, that CH-105 exhibits an activity of the same range as the known active prostaglandin antagonist aspirin for the CH-105 as an oedema inhibitor or a vessel wall permeability reducing agent (Vane, J. R. Hospital Practice, 7, 61 (1972). Favorable properties were found in tests carried out by the method of Northover (J. Path, Bect. 85, 365, 1963).

TABLE 3

| Substance | Dose mg/kg | Antiphlogistic activity (%) | | |
|---|---|---|---|---|
| | | 1 hour | 2 hours | 24 hours |
| CH-105 | 100 | 40 | 55 | 30 |
| Mebron | 100 | 23 | 23 | 0 |
| Phenylbutazone | 100 | 18 | 20 | 0 |

The significant antiphlogistic activity of CH-105 is advantageously accompanied by analgesic activity. The modified writhing test (Witkin et al.: J. Pharm. exp. Ther. 113, 400 (1961)) gave the following results:

TABLE 4

| Substance | $ED_{50}$ mg/kg | Therapeutical index |
|---|---|---|
| CH-105 | 70 | 14 |
| Mebron | 380 | 4.3 |
| Phenylbutazone | 63 | 5.5 |

TABLE 4-continued

| Substance | $ED_{50}$ mg/kg | Therapeutical index |
|---|---|---|
| Indomethacin | 2.4 | 12 |

The obtained results show the favorable toxicity of CH-105.

TABLE 5

| Substance | $LD_{50}$ mg/kg per os | |
|---|---|---|
| | rats | mice |
| CH-105 | 750 | 975 |
| Aspirin | 1600 | 1100 |
| Phenylbutazone | 770 | 350 |

In the course of clinical tests, CH-105 did not prove to be ulcerogenic, the substance was administered to one month old rats in a dose of 50 mg/kg. On the basis of our investigations CH-105 is a significant antiphlogistic also possessing antianalgesic activity and a favorable therapeutic index.

The compounds of the formula I can be used as active ingredients in pharmaceutical compositions, admixed with inert, non-toxic solid or semi-solid diluents or carriers.

Preferred pharmaceutical forms of the present invention are solid forms, such as tablets, capsules, dragées or liquid forms, such as solutions, suspensions or emulsions.

As carriers the generally used substances, such as talcum, calcium carbonate, magnesium stearate, water, polyethylene glycol may be employed.

The compositions contain, if desired some other conventionally used excipients, such as emulsifiers, and substances promoting decomposition.

The further details of our invention can be found in the following non-limiting Examples.

EXAMPLE 1

15 g. of 1,6-dimethyl-3-carbamoyl-4-oxo-6,7,8,9-tetrahydro-4H-pyrido-(1,2a)pyrimidinium methylsulfate are heated in the mixture of 450 ml. of benzene and 50 g. of triethylamine and after cooling the mixture is allowed to stand overnight in a refrigerator. The precipitated crystals are filtered. The filtrate is evaporated. The obtained residue is recrystallized from ethanol and thus yellow 1,6-dimethyl-3-carbamoyl-4-oxo-1,6,7,8-tetrahydro-4H-pyrido(1,2a)pyrimidine is obtained. Melting point: 171°–172° C.

Analysis: calculated: C 59.71%; H 6.83%; N 18.99%. found: C 59.85%; H 6.87%; N 19.03%.

EXAMPLE 2

50 g. of 1,6-dimethyl-3-carbamoyl-4-oxo-6,7,8,9-tetrahydro-4H-pyrido(1,2a)pyridinium methylsulfate are dissolved in 150 ml. of water and the pH of the solution is adjusted to neutral by adding 13.9 g. of solid sodium bicarbonate and from the resulting 1,6-dimethyl-3-carbamoyl-9a-hydroxy-4-oxo-1,6,7,8,9,9a-hexahydro-4H-pyrido(1,2a)pyrimidine 1,6-dimethyl-3-carbamoyl-4-oxo-1,6,7,8-tetrahydro-4H-pyrido(1,2a)pyrimidine is formed by discharging water and the product is precipitated from the solution in the form of crystals.

After standing for 2 hours at room temperature the crystals are filtered, washed with water and dried. 26.5 g. of yellow crystals are obtained, melting point: 165°–171° C. The aqueous filtrate is shaken out with chloroform and the chloroform solution is evaporated and a further 1.8 g. of yellow crystals are obtained, melting point: 162°–168° C.

Total yield: 86%. The combined crystalline substance is recrystallized from ethanol and thus the melting point of the resulting 1,6-dimethyl-3-carbamoyl-4-oxo-1,6,7,8-tetrahydro-4H-pyrido(1,2a)pyrimidine is raised to 170°–172° C. There is no decrease in the melting point compared with the product of Example I.

EXAMPLE 3

15.3 g. of 1,6-dimethyl-3-(N-acetyl-carbamoyl)-4-oxo-6,7,8,9-tetrahydro-4H-pyrido(1,2a)pyridinium methyl sulfate are dissolved in 50 ml. of water. The solution is neutralized with a 5% sodium carbonate solution and thus 1,6-dimethyl-3-(N-acetyl-carbamoyl)-9a-hydroxy-4-oxo-1,6,7,8,9,9a-hexahydro-4H-pyrido(1,2a)pyrimidine is formed which is converted to 1,6-dimethyl-3-(N-acetyl-carbamoyl)-4-oxo-1,6,7,8-tetrahydro-4H-pyrido(1,2a)pyrimidine by discharge of water and it is precipitated from the aqueous solution. The precipitated yellow crystals are filtered, covered with water, and dried. 9.2 g. (86%) of the product is obtained, melting point: 182°–184° C. After recrystallization from ethanol the melting point of the resulting 1,6-dimethyl-3-(N-acetyl-carbamoyl)-4-oxo-1,6,7,8-tetrahydro-4H-pyrido-(1,2a)pyrimidine is 183°–185° C.

Analysis: calculated: C 59.30%; H 6.51%; N 15.96%. found: C 59.80%; H 6.64%; N 15.68%.

EXAMPLE 4

6.38 g. of 1-methyl-3-carbamoyl-4-oxo-6,7,8,9-tetrahydro-4H-pyrido(1,2a)pyrimidinium methyl sulfate are dissolved in 50 ml. of water. The solution is neutralized with solid potassium carbonate and thus 1-methyl-3-carbamoyl-9a-hydroxy-4-oxo-1,6,7,8,9,9a-hexahydro-4H-pyrido(1,2a)-pyrimidine is obtained which is transferred under discharge of water to 1-methyl-3-carbamoyl-4-oxo-1,6,7,8-tetrahydro-4H-pyrido(1,2a)pyrimidine which is precipitated in crystalline form. The yellow crystals are filtered, covered with water and dried. 3.9 g. (94%) of yellow substance is obtained. After recrystallization the melting point of the obtained 1-methyl-3-carbamoyl-4-oxo-1,6,7,8-tetrahydro-4H-pyrido(1,2a)pyrimide is 241°–242° C.

Analysis: calculated: C 57.96%; H 6.32%; N 20.28%. found: C 58.09%; H 6.27%; N 20.25%.

Example 5

0.89 g. (4 mmoles) of 1,6-dimethyl-3-carboxy-4-oxo-1,6,7,8-tetrahydro-4H-pyrido(1,2a)pyrimidine are dissolved in 10 ml. of chloroform and 0.62 ml (4.4 mmoles) of chloroformic acid ethyl ester is added dropwise to the mixture under stirring. After stirring for ten minutes a solution of 0.70 g. (4.2 mmoles) of glycine tertiary butyl ester hydrochloride and 0.58 ml (4.2 mmole) of triethylamine in 10 ml. of chloroform are added maintaining the temperature during the addition and for an hour after the addition at −5° to −10° C. The reaction mixture is allowed to stand overnight in the refrigerator, washed three times with 5% sodium bicarbonate and three times with water, dried over sodium sulfate and dried. The residual dark yellow resinuous product is dissolved in the mixture of 5 ml. of ethyl acetate: pyridine:glacial acetic acid: water=240:20:6:11 and the solution is subjected to chromatography on a Kieselgel 60 column of size 50 cm, diameter: 1.8 cm. and of a particle size 0.063–0.125. Eluent solvent: ethyl acetate:-pyridine; glacial acetic acid:water=240:20:6:11, flow rate: 30 ml. per hour. The solvent, which is passed through the column is evaporated in vacuo and after evaporation in vacuo the residue is held for a while in vacuo of $10^{-2}$ Hgmm, to remove the pyridine acetate of the solvent. 1.00 g. of colored amorphous resinous substance is obtained, which is dissolved in 10 ml. of ethyl acetate and while still warm, 15 ml. of cyclohexane is added. The precipitated crystals are filtered and air-dried, the following day. 1.8 g. (60%) of 1,6-dimethyl-3-[(N-tert.butoxycarbonyl-methyl)-carbamoyl]-4-oxo-1,6,7,8-tetrahydro-4H-pyrido(1,2a)pyrimidine of a melting point 180°–182° C. is obtained.

Analysis: calculated: C 60.88%; H 7.51%; N 12.53%. found: C 61.12% H 7.70%; N 11.94%.

Example 6

4.4 g. (0.02 moles) of 1.6 dimethyl-3-carboxy-4-oxo-1,6,7,8-tetrahydro-4H-pyrido(1,2)pyrimidine and 3.1 ml. (0.022 mole) of triethylamine are dissolved in 50 ml of chloroform and the resulting solution is cooled to −10° C. 2.1 ml (0.022 mole) of chlorormic acid ethyl ester is added dropwise to the solution. After stirring for a further ten minutes a solution of 1.95 g. (0.022 mole) of aniline in 25 ml. of chloroform is added to the mixture, and the temperature is maintained during the addition and after the addition for an hour at −5° C. to −10° C. The reaction mixture is allowed to stand overnight in a refrigerator and the mixture is then shaken out 3 times with a 5% solution of sodium bicarbonate and then 3 times with water. The chloroform solution is dried over sodium sulfate and evaporate in vacuo. 5.7 g. (96%) of yellow crystals of a melting point of 180° C. is obtained. After recrystallization twice from ethanol 1,6-dimethyl-3-(N-phenylcarbamoyl)-4-oxo-1,6,7,8-tetrahydro-4H-pyrido(1,2a)pyrimidine is obtained, melting point: 189°–190° C.

Analysis: calculated: C 68.67%; H 6.44%; N 14.13%. found: C 68.60%; H 6.50%; N 14.21%.

Example 7

4.4 g. (0.02 moles) of 1,6-dimethyl-3-carboxy-4-oxo-1,6,7,8-tetrahydro-4H-pyrido(1,2a)pyrimidine and 3.1 ml. (0.022 mole) of triethylamine are dissolved in 50 ml. of chloroform. The solution is cooled to −10° C. and 2.1 ml. (0.022 mole) of chloroformic acid ethyl ester is added to the solution, whereafter 1.5 g. (0.022 mole) of methylamine hydrochloride suspended in 25.0 ml. of chloroform and 3.1 ml. of triethylamine are also added. The solution is stirred for 1 hour at a temperature of −5° C. to −10° C. an the mixture is then allowed to stand overnight in a refrigerator. The reaction mixture is then shaken out the following day 3 times with 50 ml. of a 5% aqueous solution of sodium carbonate and then with 50 ml. of water. The chloroform solution is dried over sodium sulfate and evaporated. 3.9 g. (83%) of yellow product is obtained. After recrystallization from ethanol 1,6-dimethyl-3-(N-methyl-carbamoyl)-4-oxo-1,6,7,8,-tetrahydro-4H-pyrido(1,2a)pyrimidine is obtained, melting point: 172°–174° C.

Analysis: calculated: C 61.26%; H 7.28%; N 17.86%. found: C 61.08%; H 7.40% N 17.75%.

Example 8

4.4 g. (0.02 mole) of 1,6-dimethyl-3-carboxy-4-oxo-1,6,7,8-tetrahydro-4H-pyrido(1,2a)pyrimidine and 3.1 ml. of triethylamine are dissolved in 50 ml. of chloroform and 2.1 ml. (0.022 mole) of chloroformic acid ethyl ester and 1.9 g. (0.022 mole) of piperidine dissolved in 25 ml. of chloroform are added dropwise at −10° C. to the solution. The reaction mixture is stirred for a further hour at −5° C. to −10° C. and it is allowed to stand overnight in a refrigerator.

The following day the chloroform solution is three times shaken out with 50 ml. of a 5% solution of sodium bicarbonate and dried over sodium sulfate, and evaporated. 5.2 g. (90%) of 1,6-dimethyl-4-oxo-3-(piperidyl-carbonyl)-1,6,7,8-tetrahydro-4H-pyrido(1,2a)pyrimidine is obtained in the form of yellow incrystallizable oil.

Analysis: calculated: C 66.41%; H 8.01%; N 14.52%. found: C 66.58%; H 8.20%; N 14.47%.

Example 9

4.44 g. (0.02 mole) of 1.6-dimethyl-3-carboxy-4-oxo-1,6,7,8-tetrahydro-4H-pyrido(1,2a)pyrimidine and 3.1 ml. of triethylamine are dissolved in 50 ml. of chloroform and 2.1 ml. (0.022 mole) of chloroformic acid ethyl ester and 5.26 g. (0.022 mole) of diphenylpropylamine dissolved in 25 ml. of chloroform are added dropwise at −10° C. to the solution. The reaction mixture is then stirred for 1 hour at a temperature of −5° C. to −10° C. and the mixture is then allowed to stand overnight in a refrigerator. The following day the chloroform solution is shaken out with a 5% sodium bicarbonate solution and with water, dried over sodium sulfate and evaporated. 6.8 g. (82%) of yellow crystals are obtained. After recrystallization from ethanol 1,6-dimethyl-3-[N-(3,3-diphenyl-propyl)-carbamoyl]-4-oxo-1,6,7,8-tetrahydro-4H-pyrido(1,2a)pyrimidine of a melting point of 173°–175° C. is obtained.

Analysis: calculated: C 75.15%; H 7.04%; N 10.11%. found: C 74.92%; H 6.96%; N 9.84%.

Example 10

4.44 g. of 1,6-dimethyl-3-carboxy-4-oxo-1,6,7,8-tetrahydro-4H-pyrido(1,2a)pyrimidine and 3.1 ml. of triethylamine are dissolved in chloroform at −10° C. and 2.1 ml. of chloroformic acid ethyl ester and 1.6 g. of tert. butylamine in chloroform are added to the solution. The reaction mixture is stirred at a temperature of −5°C. to −10° C. and it is allowed to stand overnight in a refrigerator. The following day the chloroform solution is shaken out with a 5% sodium bicarbonate solution and then with water, dried over sodium sulfate, filtered and evaporated. 5.3 g. (95%) of yellow crystals are obtained. After recrystallization from ethanol 1,6-dimethyl-3-(N-tert-butyl-carbamoyl)-4-oxo-1,6,7,8-tetrahydro-4H-pyrido(1,2a)pyrimidine is obtained, melting point: 179°–181° C.

Analysis: calculated: C 64.96%; H 8.36%; N 15.15%. found; C 64.68%; H 8.32%; N 15.42%.

Example 11

4.44 g. of 1,6-dimethyl-3-carboxy-4-oxo-1,6,7,8-tetrahydro-4H-pyrido(1,2a)pyrimidine and 3.1 ml. of triethylamine are dissolved in chloroform and 2.1 ml. of chloroformic acid ethyl ester and 2.7 g. of beta-phenylethylamine are added to the solution at −10° C. The reaction mixture is stirred for 1 hour at a temperature of −5° C. to −10° C. and then allowed to stand overnight in a refrigerator. The following day the chloroform solution is shaken out with a 5% solution of sodium bicarbonate and then with water, dried over sodium sulfate, filtered and evaporated. 2.1 g. of yellow crystals are obtained. After recrystallization from ethanol 1,6-dimethyl-3-[N-(2-phenyl-ethyl)-carbamoyl]-4-oxo-1,6,7,8-tetrahydro-4H-pyrido(1,2a)pyrimidine is obtained, melting point: 141°–143° C.

Analysis: Calculated: C 70.13%; H 7.12%; N 12.91%. found: C 69.83%; H 6.96%; N 12.74%.

Example 12

According to the method described in Example 2 but using (−)-1,6-dimethyl-3-carbamoyl-4-oxo-6,7,8,9-tetrahydro-4H-pyrido(1,2a)pyrimidinium-methylsulfate $[(\alpha)_D^{20}=-59°, (c=2, methanol)]$ as starting material (+)-1,6-dimethyl-3-carbamoyl-4-oxo-1,6,7,8-tetrahydro-4H-pyrido(1,2a)pyrimidine is obtained, melting point: 171°–173° C. $[(\alpha)_D^{20}=+71°(c=2, methanol)]$.

Analysis: Calculated: C 59.71%; H 6.83%; N 18.99%. found: C 59.69%; H 6.78%; N 19.04%.

EXAMPLE 13

According to the method described in Example 2 but using (+)-1,6-dimethyl-3-carbamoyl-4-oxo-6,7,8,9-tetrahydro-4H-pyrido(1,2a)pyrimidine methosulfate $[(\alpha)_D^{20}=+58.5°(c=2, methanol)]$ as starting material (−)-1,6-dimethyl-3-carbamoyl-4-oxo-1,6,7,8-tetrahydro-4H-pyrido(1,2a)pyrimidine is obtained. $[(\alpha)_D^{20}=-70°, methanol)]$.

Analysis: calculated: C 59.71% H 6.83%; N 18.99%. found: C 59.85%; H 6.90%; N 18.92%.

Example 14 0,1 g capsule

Composition for 5000 capsules:

| | | |
|---|---|---|
| (a.) | 3-carbamoyl-1,6-dimethyl-4-oxo-1,6,7,8--tetrahydro-4H-pyrido(1,2a)-pyrimidine(CH-105) | 500 g |
| (b.) | Potato starch | 115 g |
| (c.) | Gelatine | 5 g |
| (d.) | Distilled water | 30 g |
| (e.) | 2 N hydrochloric acid | 5 g |
| (f.) | Ethylalcohol(90%) | 60 g |
| (g.) | Potato starch | 25 g |
| (h.) | Talc | 25 g |
| (i.) | Stearic acid | 5 g |

Method

The powder mixture of components (a.) and (b.) is moistened with the solution of components (c.)-(f.) in a suitable kneading-mixing machine, thereafter it is granulated through a 0.3 mm mesh screen and dried at 40° C. The granules thus obtained are regranulated through a 0.15 mm mesh screen. It is admixed with the homogeneous powder mixture of components (g.)-(i.) and filled into hard gelatine capsules in a suitable filling machine. Weight of a capsule: 0.133 g. The finished capsules are packed in a conventional manner.

Example 15 0.1 g tablet, coated pill, dragée.

Composition for 5000 tablets
See Example 14.
Method

The granules prepared according to Example 14 are pressed into tablets in a suitable tabletting machine, weight of a tablet: 0.133 g. The finished tablets are per se furnished with a film coating, or they are formed into dragée with a sugar layer.

EXAMPLE 16

0.4 g tablets of coated pills of prolonged effect.

| Composition for 1000 tablets. | |
| --- | --- |
| CH-105 active ingredient | 400 g |
| Crystalline cellulose | 160 g |
| Eudragit lacque | 7 g |
| Potato starch | 35 g |
| Talc | 22 g |
| Magnesium stearate | 6 g |

Method

The mixture of the active ingredient and the crystalline cellulose is granulated by the propanol solution of the Eudragit lacque in a conventional manner. The homogeneous powder mixture of potato starch, talc and magnesium stearate is admixed with the dried and regranulated product and is formed into tablets weighing 0.63 g under high pressure. The tablets thus obtained may be furnished with film- or sugar layer in a manner known per se.

EXAMPLE 17

50 mg injection

| Composition for 10,000 ampules | |
| --- | --- |
| CH-105 | 500 g |
| Sodium chloride | 17 g |
| Sodium pyrosulphite | 3 g |
| Filled up to 10,000 cm³ with distilled water | |

Method

In a container suitable for injection purposes the solution corresponding to the above composition is prepared in a manner known per se. The nearly isotonic and isohydric solution is filled into ampoules of 1.1 cm³ under nitrogen. The sterilization is performed for 30 minutes at 120° C.

EXAMPLE 18

0.15 g suppository

| Composition for 1000 suppositories. | |
| --- | --- |
| CH-105 | 150 g |
| Suppository mass | 2.350 g |

Method

The molten suppository mass is dried over about 60 g of anhydrous sodium sulphate. The active ingredient is homogenized with the filtered suppository mass until warm. The suppositories are formed in a suitable machine, and are packed in a conventional manner. As the suppository mass cocoa-butter or synthetic base substances may be used.

EXAMPLE 19

2% ointment

| Composition for 1000 g of ointment | |
| --- | --- |
| CH-105 | 20 g |
| Methyl cellulose | 50 g |
| Glycerol | 100 g |
| Methyl—p-hydroxy-benzoate | 0;5 g |

| Composition for 1000 g of ointment | |
| --- | --- |
| Propyl—p-hydroxy-benzoate | 0;3 g |
| Essence of perfume | quantum satis |
| Distilled water for supplementing the mixture to 1000 g. | |

Method

The methyl- and propyl-p-hydroxy-benzoates are dissolved in glycerol. Homogenized with swelled methyl cellulose the active ingredient and the essence of perfume are dissolved. The finished product is made up with water to 1000 g, and filled into hermethic containers in a conventional manner.

EXAMPLE 20

| Composition for 1000 combination suppositories | |
| --- | --- |
| CH-105 | 75 g |
| Diethyl barbituric acid | 15 g |
| Routine | 20 g |
| Nicotinic amide | 25 g |
| Witepsol-H mass | 1.865 g |

Method

The active ingredient is homogenized with diethyl barbituric acid in a kneading-mixing machine. The routine and the nicotinic amide are homogenized with the mass, thereafter it is homogenized with small portions of the suppository mass, dried over anhydrous sodium sulphate in the melt. The suppositories weighing 2 g are formed in a suitable machine.

EXAMPLE 21

Tablet, coated pill, dragees

| Composition for 1000 tablets, coated pills, dragees | |
| --- | --- |
| CH-105 | 50 g |
| Indomethacine | 10 g |
| Crystalline cellulose | 35 g |
| Polivinylpyrrolidone | 5 g |
| Colloidal silicic acid | 3 g |
| Talc | 2 g |
| Magnesium stearate | 2 g |

Method

The active inredient and indomethacine are mixed with crystalline cellulose and polyvinylpyrrolidone and passed through a 0.15 mm mesh screen. After mixing with a fine powder mixture of colloidal silicic acid, talc and magnesium stearate the product is directly pressed into tablets weighing 0.107 g.

Remarks

According to the above examples, other active substances e.g. alkaloid-type analgesics, dionine, codeine may be made finished into tablets in a similar way in combination with CH-105.

What we claim is:

1. (±) 1,6-Dimethyl-3-carbamoyl-4-oxo-1,6,7,8-tetrahydro-4H-pyrido(1,2a)pyrimidine.

2. (+) 1,6-Dimethyl-3-carbamoyl-4-oxo-1,6,7,8-tetrahydro-4H-pyrido(1,2a)pyrimidine.

3. (−) 1,6-Dimethyl-3-carbamoyl-4-oxo-1,6,7,8-tetrahydro-4H-pyrido(1,2a)pyrimidine.

4. 1,6-Dimethyl-3-(N-tert-butyl-carbamoyl)-4-oxo-1,6,7,8-tetrahydro-4H-pyrido(1,2-a)pyrimidine.

* * * * *